United States Patent
Kurd et al.

(10) Patent No.: US 10,463,362 B2
(45) Date of Patent: Nov. 5, 2019

(54) DEVICES AND METHODS FOR SUTURE PLACEMENT

(71) Applicant: Dura Tap LLC, Wayne, PA (US)

(72) Inventors: Mark F. Kurd, Bryn Mawr, PA (US); David Greg Anderson, Moorestown, NJ (US); Jens Johnson, Austin, TX (US); Jay Tapper, Wayne, PA (US)

(73) Assignee: DURASTAT LLC, Wayne, PA (US)

( * ) Notice: Subject to any disclaimer, the term of this patent is extended or adjusted under 35 U.S.C. 154(b) by 317 days.

(21) Appl. No.: 15/489,939

(22) Filed: Apr. 18, 2017

(65) Prior Publication Data

US 2018/0296208 A1 Oct. 18, 2018

(51) Int. Cl.
- A61B 17/04 (2006.01)
- A61B 17/06 (2006.01)
- A61B 17/00 (2006.01)

(52) U.S. Cl.
CPC ...... *A61B 17/0469* (2013.01); *A61B 17/0482* (2013.01); *A61B 17/0491* (2013.01); *A61B 17/06066* (2013.01); *A61B 2017/00367* (2013.01); *A61B 2017/00738* (2013.01); *A61B 2017/00946* (2013.01);
(Continued)

(58) Field of Classification Search
CPC ............ A61B 17/0469; A61B 17/0482; A61B 17/0491; A61B 17/06066; A61B 2017/00367; A61B 2017/00738; A61B 2017/00946; A61B 2017/047; A61B 2017/06052; A61B 2017/06095; A61B 2017/0609
See application file for complete search history.

(56) References Cited

U.S. PATENT DOCUMENTS

| | | | |
|---|---|---|---|
| 4,752,024 A * | 6/1988 | Green | A61B 17/115 227/19 |
| 5,860,992 A * | 1/1999 | Daniel | A61B 17/0469 606/139 |
| 6,397,108 B1 | 5/2002 | Camps | |

(Continued)

FOREIGN PATENT DOCUMENTS

WO 96/09796 4/1996

OTHER PUBLICATIONS

International Search Report filed in PCT/US18/27711 dated Jul. 5, 2018.
(Continued)

*Primary Examiner* — Jocelin C Tanner
(74) *Attorney, Agent, or Firm* — Rankin, Hill & Clark LLP (57) ABSTRACT

A suturing device includes a handle, an elongate body, an actuator and a needle holder. The handle includes a proximal handle end and a distal handle end. The elongate body connects with the handle and includes a proximal end portion and a distal end portion. The actuator is operable between a first operating position and a second operating position. The actuator includes a manually operated member including an operator contact surface spaced from the proximal handle end in a direction toward the distal handle end. The needle holder includes a distal end section having a distal-most tip and defines a needle passage and a distal opening adjacent the distal-most tip. The needle passage is configured to receive at least a portion of an associated needle when the actuator is in the first operating position.

5 Claims, 8 Drawing Sheets

(52) U.S. Cl.
CPC ............... *A61B 2017/047* (2013.01); *A61B 2017/06052* (2013.01); *A61B 2017/06095* (2013.01)

(56) References Cited

U.S. PATENT DOCUMENTS

| | | | |
|---|---|---|---|
| 7,097,375 B1 | 8/2006 | Bui | |
| 2002/0156422 A1* | 10/2002 | Takagi | A61M 25/0631 604/164.12 |
| 2002/0183839 A1* | 12/2002 | Garrison | A61B 17/00234 623/2.11 |
| 2003/0083620 A1* | 5/2003 | Luther | A61M 25/0606 604/164.07 |
| 2003/0083682 A1* | 5/2003 | Heise | A61B 17/320068 606/169 |
| 2004/0167547 A1 | 8/2004 | Beane | |
| 2007/0073322 A1 | 3/2007 | Mikkaichi | |
| 2010/0069940 A1* | 3/2010 | Miller | A61B 17/320068 606/169 |
| 2012/0116422 A1* | 5/2012 | Triplett | A61B 17/0469 606/144 |

OTHER PUBLICATIONS

"FG-600U Disposable 3 prong grasping forceps" by Olympus, available on Mar. 17, 2016, olympusaustralia.com.au/product/detail/151/FG-600U-Disposable-3-prong-grasping-forceps>I; figure.

* cited by examiner

DEVICES AND METHODS FOR SUTURE PLACEMENT

BACKGROUND

The present disclosure relates generally to surgery and the placement of sutures, and more particularly, to devices and methods for the suture repair of tissue.

Surgical closure techniques using sutures is one approach to tissue repair. In some instances, however, these techniques can be difficult to execute due to anatomic constraints, obstruction of visualization by blood or other bodily fluids, and the proximity to nerve rootlets. In some instances, these challenges can be further complicated when using minimally invasive techniques such as, for example, a tubular retractor. Traditional tools and devices can be limited and, in some instances, lack maneuverability to avoid obstructions and/or to enable adequate passage of the needle and suture through the tissue.

SUMMARY

In view of the foregoing a suturing device includes a handle, an elongate body, an actuator and a needle holder. The handle includes a proximal handle end and a distal handle end. The elongate body connects with the handle and includes a proximal end portion and a distal end portion. The actuator interacts with the elongate body and is operable between a first operating position and a second operating position. The actuator includes a manually operated member including an operator contact surface spaced from the proximal handle end in a direction toward the distal handle end. The needle holder extends away from the distal end portion or is provided as part of the distal end portion of the elongate body. The needle holder includes a distal end section having a distal-most tip and defines a needle passage and a distal opening adjacent the distal-most tip. The needle passage is configured to receive at least a portion of an associated needle when the actuator is in the first operating position.

DETAILED DESCRIPTION

Figure 1:
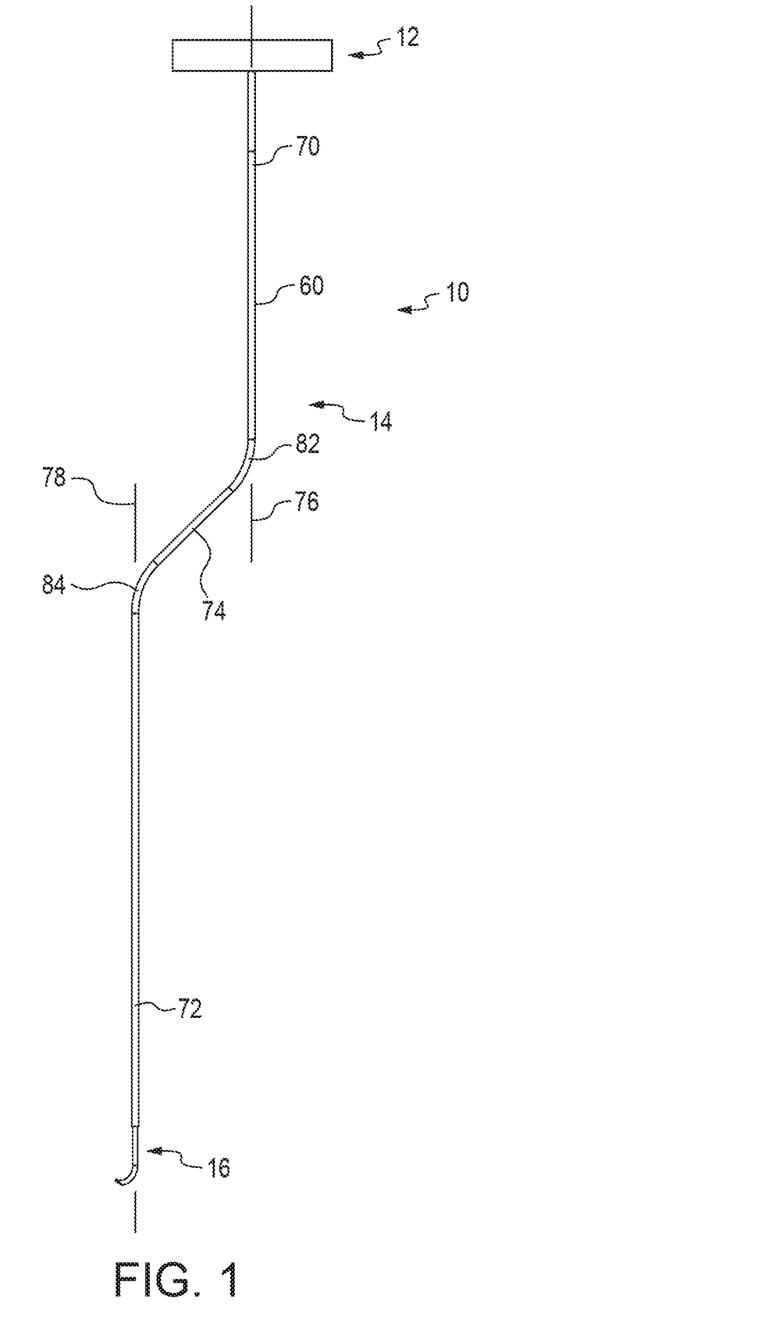
FIG. 1 is a side view a suturing device.
Figure 2:
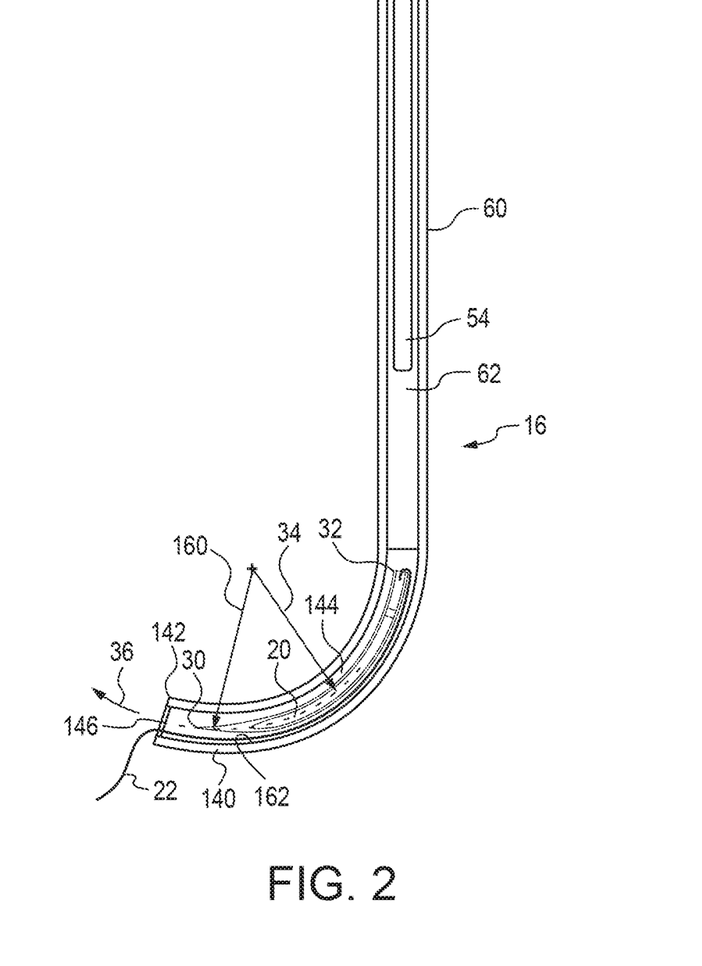
FIG. 2 is a cross—sectional view of a lower portion of the suturing device of FIG. 1.

FIG. 1 depicts an example of a suturing device 10 that is useful to suture tears in tissue that can be used in many different types of surgical procedures. The suturing device 10 generally includes an actuator 12, an elongate body 14, and a needle holder 16. The suturing device 10 is particularly useful during a minimally invasive surgical procedure that is performed through a tubular retractor or other small surgical portal to accurately locate a needle 20 and a suture 22, which are shown in FIG. 2.

The needle 20 in the illustrated embodiment is a curved needle having a first end 30, which is pointed, and a second end 32, which is opposite to the first end 30. The needle 20 can be similar to commercially available curved needles made from known materials. The needle 20 can be formed having a curved needle radius 34. The needle 20 could also be formed from a malleable, or flexible, material such that the needle 20 could follow a curve when positioned within the needle holder 16, which is curved, and then later straighten after exiting the needle holder 16. Both the needle holder 16 and the needle 20 can take other configurations, such as straight.

Actuation of the actuator 12 moves the needle 20 in an advance direction 36 with respect to the needle holder 16. The needle 20 moves from a retracted position, which is shown in FIG. 2, to a released condition in which the needle 20 is released from the needle holder 16. When in the released condition, the surgeon can grasp the needle 20, for example with forceps, and pull the needle 20 and the suture 22. The suture 22 connects with the needle 20 and extends from the second end 32 of the needle 20. The suture 22 can be swaged to the second end 32 of the needle 20. The suture 22 can also connect with the needle 20 in other conventional manners. The suture 22 can be acquired from known suture manufacturers.

The actuator 12 is operable between a first operating position and a second operating position. Movement of the actuator 12 from the first operating position toward the second operating position moves the needle 20 in the advance direction 36 with respect to the needle holder 16 thus moving the needle 20 toward the released condition in which the needle 20 is released from the needle holder 16. The actuator 12 includes a manually operated member, variations of which will be described in more detail, connected with a wire 54 (FIG. 2). The manually operated member could connect with the wire 54 through a tube, rod or other element if desired. In the illustrated embodiment, the actuator 12 includes a flexible section, which in the illustrated embodiment is made up of the wire 54, which can be made from nitinol. The flexible section is configured to bend within the needle holder 16 when the actuator 12 is moved from the first operating position toward the second operating position. The manually operated member connects with the wire 54 such that movement of the manually operated member results in movement of the wire 54.

The elongate body 14 in the illustrated embodiment is in the form of a cannula. The elongate body 14 has an outer surface 60, which is smooth, and defines a track 62 that receives a portion of the actuator 12. Similar to the embodiment described above, the elongate body 14 is a cannula and the track 62 is a lumen that receives the wire 54 of the actuator 12. The track 62 need not encircle the wire 54, but could be U-shaped. In the depicted embodiments, the elongate body 14 is circular in a cross section taken normal to the longest dimension of the elongate body 14, however, the elongate body 14 could take alternative configurations, such as polygonal or U-shaped.

The elongate body 14 includes the proximal end portion 70 and a distal end portion 72. The proximal end portion 70 connects with the actuator 12, or, if desired, the proximal end portion 70 can connect with a handle in a manner that will be described in more detail below. In the illustrated embodiment, the needle holder 16 is received in and connected with the elongate body 14 and extends away from the distal end portion 72. Alternatively, the needle holder 16 can be provided as part of the distal end portion 72 of the elongate body 14. The elongate body 14 is made from a rigid metal material; however, if desired at least a portion of the elongate body 14 may be made from a malleable or flexible material to allow the surgeon to bend at least a portion of the elongate body 14 into a desirable configuration for insertion into an animal body during a surgical procedure. In the illustrated embodiment, an outer diameter of the elongate body 14 is constant between the proximal end portion 70 and the distal end portion 72. The outer diameter can be less than 3.5 mm, which provides a very slim device to enhance the line of sight for a surgeon during the surgical procedure.

The elongate body 14 has a bayonet configuration in the illustrated embodiments; however, the elongate body could take alternative configurations, such as straight along a longitudinal axis. The elongate body 14 includes an intermediate portion 74 positioned between the proximal end portion 70 and the distal end portion 72. The proximal end portion 70 extends along a proximal end portion longitudinal axis 76. The distal end portion 72 extends along a distal end portion longitudinal axis 78, which is offset from the proximal end portion longitudinal axis 76 in a forward direction. In the illustrated embodiment, the distal end portion longitudinal axis 78 is offset from the proximal end portion longitudinal axis 76 about 25 mm. The proximal end portion 70 transitions to the intermediate portion 74 through a proximal bend 82 and the intermediate portion 74 transitions to the distal end portion 72 through a distal bend 84. In the illustrated embodiment, the proximal bend 82 and the distal bend 84 are both angled internally 135 degrees.

The needle holder 16 extends away from the distal end portion 72 or is provided as part of the distal end portion 72 of the elongate body 14. With reference to FIG. 2, the needle holder 16 is a hollow tubular member. In the illustrated embodiment, a portion of the needle holder 16 that is aligned with the distal end portion longitudinal axis 78 is received inside the elongate body 14; however, the needle holder 16 could be formed as part of the elongate body, e.g., both the elongate body 14 and the needle holder 16 could be made from one tubular stock material. The needle holder 16 depicted in the illustrated embodiment is a curved needle holder that generally follows a constant radius such that the suturing device 10 can have J-hook configuration at a distal end thereof. In the illustrated embodiment, the needle holder 16 is not intended to be removable from the elongate body 14; however, in an alternative arrangement the needle holder 16 can selectively connect with the elongate body 14 via a mechanical connection such as a friction fit or a bayonet connection.

With reference to FIG. 2, the needle holder 16 includes a distal end section 140 having a distal-most tip 142. The needle holder 16 defines a needle passage 144 that is in communication with the track 120 and a distal opening 146. The distal opening 146 is offset from distal end portion longitudinal axis 78 in a forward direction. The needle passage 144 in the illustrated embodiment is curved and follows a curved needle passage radius 160, which is measured along a midline of the needle passage 144. In the embodiment depicted in FIG. 2, at least a portion of the suture 22 extends along the needle passage 144 from the second end 32 of the needle 20 toward the distal opening 146 between the needle 20 and an inner surface 162 of the needle holder 16 when the needle 20 is received in the needle passage 144 and the actuator 12 is in the first operating position.

Figure 3:
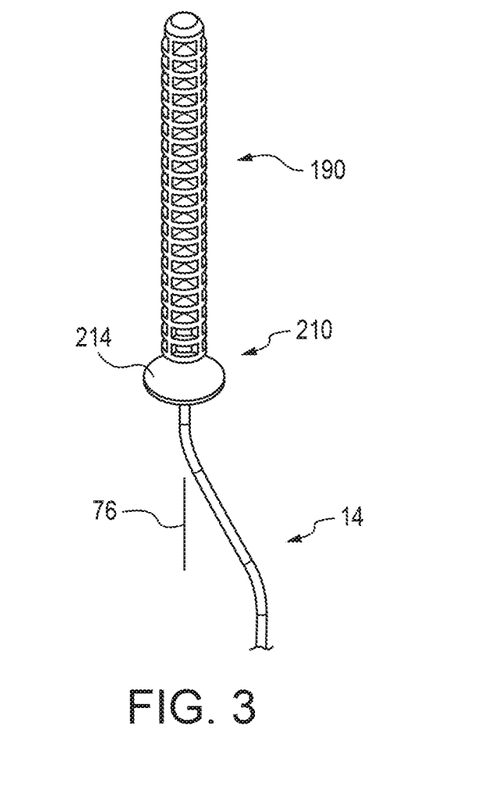
FIG. 3 is a perspective view of a handle and a proximal end portion of an elongate body showing one variation for the handle and an actuator for the suturing device of FIG. 1.
Figure 4:
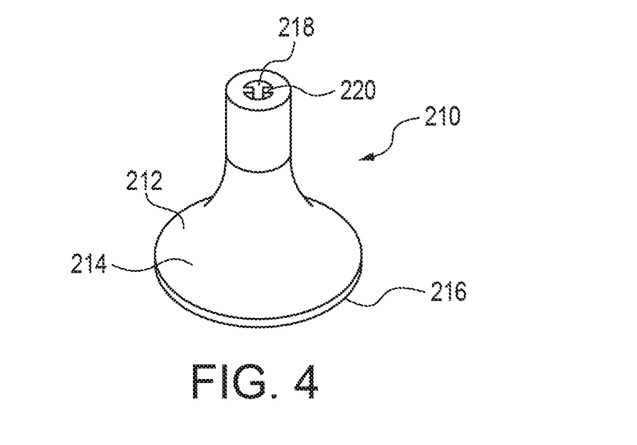
FIG. 4 is a perspective view of a slide button of the suturing device shown in FIG. 3.
Figure 5:
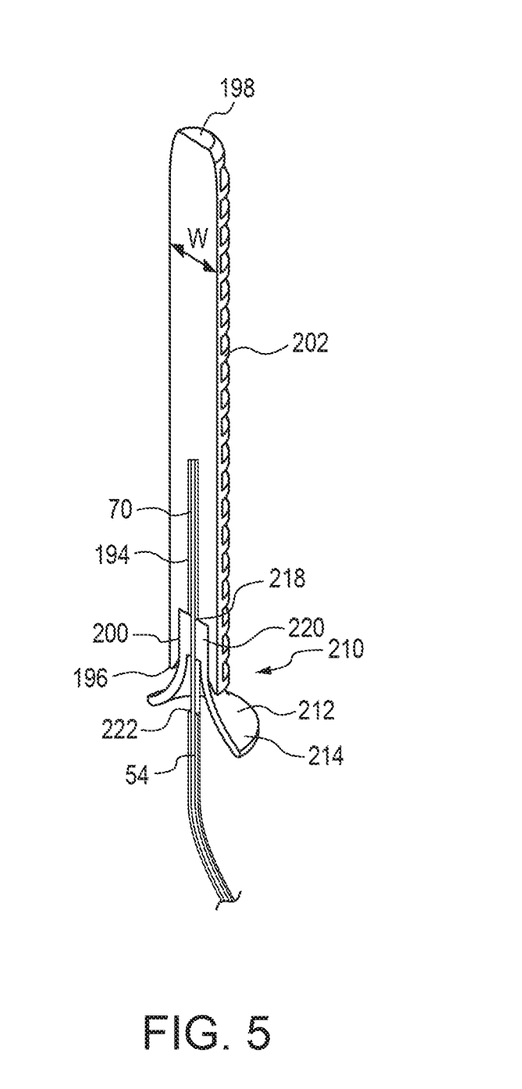
FIG. 5 is a cross—sectional view of the handle, the slide button and the proximal end portion shown in FIG. 3.
Figure 6:
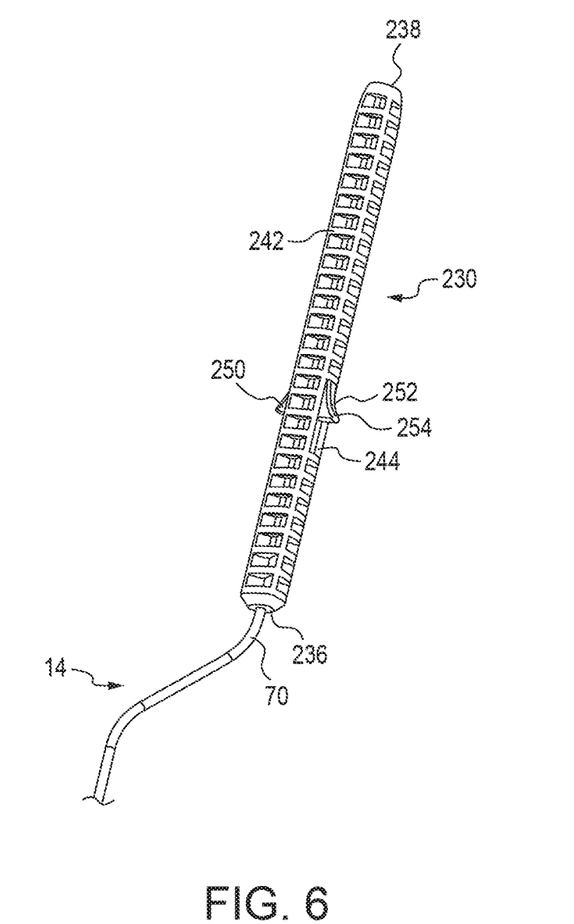
FIG. 6 is a perspective view of another handle and the proximal end portion of an elongate body of the suturing device showing another variation for the handle and an actuator for the suturing device of FIG. 1.

With reference to FIGS. 3-5, the suturing device 10 can also include a handle 190 connected with the elongate body 14. The handle 190 connects with a proximal end portion 70 of the elongate body 14 and is fixed to the elongate body 14 such that movement of the handle 190, e.g., rotational or translational movement, results in the same movement of the elongate body 14. The handle 190 includes an elongate bore 194 in which the proximal end portion 70 of the elongate body 14 is received. The elongate bore 194 extends from a distal handle end 196 toward a proximal handle end 198 and is aligned with the proximal end portion longitudinal axis 76. The elongate bore 194 in the illustrated embodiment does not extend all the way from the distal handle end 196 to the proximal handle end 198. The handle 190 also includes a slide button counter bore 200 extending inwardly from the distal handle end 196 toward the proximal handle end 198. The slide button counter bore 200 is larger in diameter than and coaxial with the elongate bore 194.

The handle 190 also defines an outer side surface 202 extending between the proximal handle end 198 and the distal handle end 196. The outer side surface 202 follows a surface of revolution about the proximal end portion longitudinal axis 76. In the illustrated embodiment, the outer side surface 102 is generally cylindrical. The maximum outer diameter of the handle 190, which can also be referred to as a width measured perpendicular to the proximal end portion longitudinal axis 76 since the handle 190 need not be circular in a cross section normal to the proximal end portion longitudinal axis 76, can be 10-20 mm. In the illustrated embodiment, the handle 190 has a width W measured perpendicular to the proximal end portion longitudinal axis 76 of less than 12 mm. Common tubular retractors used during minimally invasive surgery procedures have inner diameters measuring between 14 mm to 22 mm. The maximum width of the handle 190 is not too large, which could impede the line of sight for the surgeon during a surgical procedure, especially when the surgeon is working through a tubular retractor or another small surgical portal other than a tubular retractor.

The actuator 12 in FIGS. 3-5 includes a manually operated member, which is a slide button 210 in this embodiment, including an operator contact surface 212 spaced from the proximal handle end 198 in a direction toward the distal handle end 196. In the embodiment depicted in FIGS. 3-5, the slide button 210 is movable coaxial or parallel with the proximal end portion longitudinal axis 76. The slide button 210 includes flared section 214 extending outwardly in a radial direction from the distal handle end 196. The flared section 214 includes a peripheral edge 216 surrounding the proximal end portion longitudinal axis 76, which is the axis along which the slide button moves. The flared section 214 and the peripheral edge 216 are circular in FIGS. 3-5, but could take alternative configurations. The peripheral edge 216 extends beyond (radially outward from) the outer side surface 202 of the handle 190. The flared section 214 defines the operator contact surface 212 which is positioned forwardly (toward the distal end portion 72 of the elongate body 14) from the distal handle end 196.

The slide button 210 is connected with the wire 54 such that movement of the slide button 210 results in movement of the wire 54. The slide button 210 includes a wire receiving passage 218 that receives the wire 54. Tabs 220 extend into the wire receiving passage 218 to engage the wire 54 to connect the slide button 210 with the wire 54. The elongate body 14 includes slits 222, and a respective tab 220 extends through a respective slit 222 to provide the connection between the slide button 210 and the wire 54 with the wire being received in the elongate body 14. Instead of connecting directly with the wire 54, the slide button 210 could connect with the wire 54 through a tube, rod or other element if desired, where the tabs 220 engage the tube, rod or other element, which is connected with the wire 54.

At least a portion of the slide button 210 is received in the slide button counter bore 200 when the actuator is in the first operating position, which is shown in FIG. 5. To move the actuator to the second operating position, the operator pushes the operator contact surface 212 away from the distal handle end 196 along the proximal end portion longitudinal axis 76.

With reference to FIGS. 6-9, the suturing device 10 can include a handle 230 connected with the elongate body 14. The handle 230 connects with a proximal end portion 70 of the elongate body 14 and is fixed to the elongate body 14 such that movement of the handle 230, e.g., rotational or translational movement, results in the same movement of the elongate body 14. The handle 230 includes an elongate bore 234 in which the proximal end portion 70 of the elongate body 14 is received. The elongate bore 234 extends from a distal handle end 236 toward a proximal handle end 238 and is aligned with the proximal end portion longitudinal axis 76. The elongate bore 234 in the illustrated embodiment does not extend all the way from the distal handle end 236 to the proximal handle end 238.

The handle 230 also defines an outer side surface 242 extending between the proximal handle end 238 and the distal handle end 236. The outer side surface 242 follows a surface of revolution about the proximal end portion longitudinal axis 76. In the illustrated embodiment, the outer side surface 242 is generally cylindrical. The maximum outer diameter of the handle 230, which can also be referred to as a width measured perpendicular to the proximal end portion longitudinal axis 76 since the handle 230 need not be circular in a cross section normal to the proximal end portion longitudinal axis 76, can be 10-20 mm. In the illustrated embodiment, the handle 230 has a width W measured perpendicular to the proximal end portion longitudinal axis 76 of less than 12 mm. The handle 230 includes at least one slide button notch 244 extending inwardly from the outer side surface 242 of the handle 230. Two slide button notches 244 are provided in FIG. 6, and four slide button notches 244 (not visible in FIG. 8) would be provided in FIG. 8. The slide button notches 244 lead to a slide button cavity 246 within the handle 230.

The actuator 12 in FIGS. 6-9 includes a manually operated member, which is a slide button 250 in this embodiment, including an operator contact surface 252 spaced from the proximal handle end 238 in a direction toward the distal handle end 236. In the embodiment depicted in FIGS. 6-9, the slide button 250 is movable coaxial or parallel with the proximal end portion longitudinal axis 76. The slide button 250 slides within the slide button cavity 246 and the slide button notches 244 when the actuator is moved from the first operating position toward the second operating position.

The slide button 250 includes flared sections 254 extending outwardly in a radial direction from the outer side surface 242 of the handle 230. Each flared section 254 defines a respective operator contact surface 252 which is positioned forwardly (toward the distal end portion 72 of the elongate body 14) from the proximal handle end 238. In the embodiment depicted in FIGS. 6-9, the slide button 250 is positioned between the proximal handle end 238 and the distal handle end 236 when the actuator is in the first operating position and the second operating position.

Figure 7:
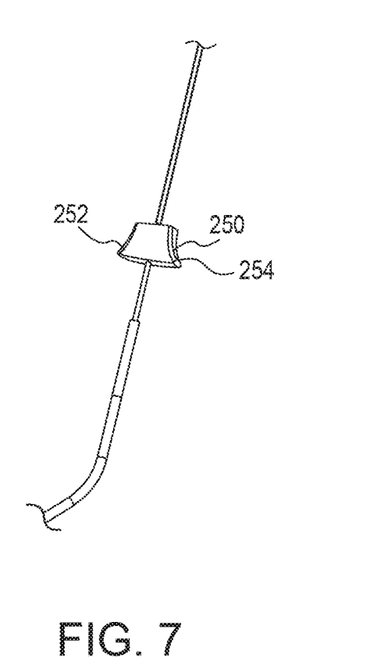
FIG. 7 is a perspective view of another slide button connected with a wire and the proximal end portion of the elongate body of the suturing device of FIG. 6.

The slide button 250 is connected with the wire 54 such that movement of the slide button 250 results in movement of the wire 54. The slide button 250 includes a wire receiving passage 256 that receives the wire 54. Instead of connecting directly with the wire 54, the slide button 250 could connect with the wire 54 through a tube, rod or other element if desired, where the slide button 250 engages the tube, rod or other element, which is connected with the wire 54.

Figure 8:
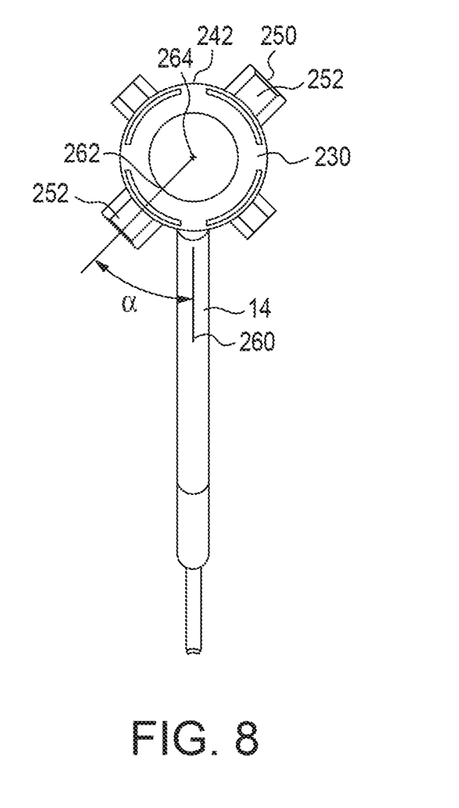
FIG. 8 is a top view of the suturing device of FIG. 1 having the handle and actuator shown in FIG. 6.
Figure 9:
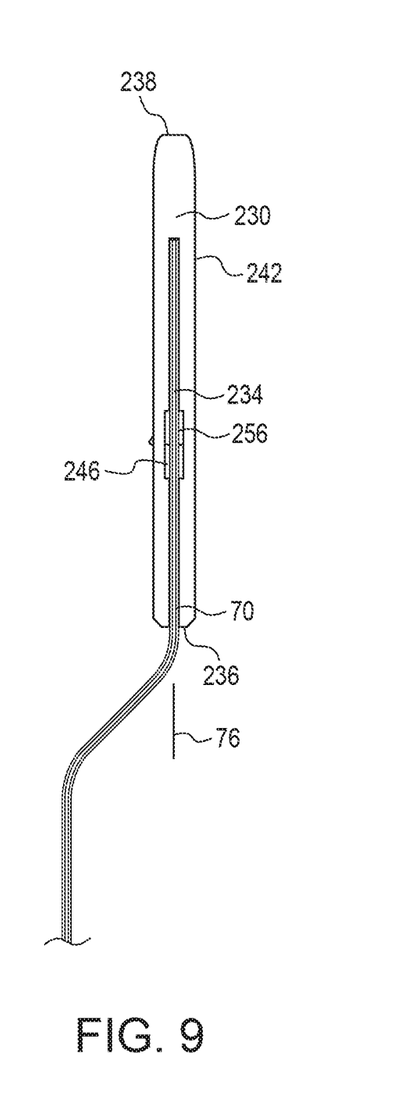
FIG. 9 is a cross—sectional view of the handle, the slide button and the proximal end portion shown in FIG. 6.

As mentioned above, the elongate body 14 can have a bayonet configuration and defines the proximal end portion longitudinal axis 76 and the distal end portion longitudinal axis 78 (see FIG. 1). With reference to FIG. 8, both the proximal end portion longitudinal axis 76 and the distal end portion longitudinal axis 78 reside in an elongate body plane 260. A line 262 emanating from the center 264 of the handle 230 through the operator contact surface 252 is offset an internal angle α from the elongate body plane 260. Alternatively, the needle holder 16 can be a curved needle holder defining a curved needle passage 144 following a curved needle passage radius 160, which is shown in FIG. 2. With reference back to FIG. 8, the line 262 emanating from the center 264 of the handle 230 through the operator contact surface 252 can be offset an internal angle α from the plane in which the curved needle passage radius 160 resides. Positioning the operator contact surface 252 as such locates the operator contact surface 252 away from the line of sight for the surgeon. The internal angle α depicted in FIG. 8 is about 45 degrees, however, the internal angle α can be between 5 degrees and 85 degrees.

FIGS. 6-9 show the actuator in the first operating position. To move the actuator to the second operating position, the operator pushes the operator contact surface 252 away from proximal handle end 238 toward the distal handle end 236 along the proximal end portion longitudinal axis 76.

Figure 10:
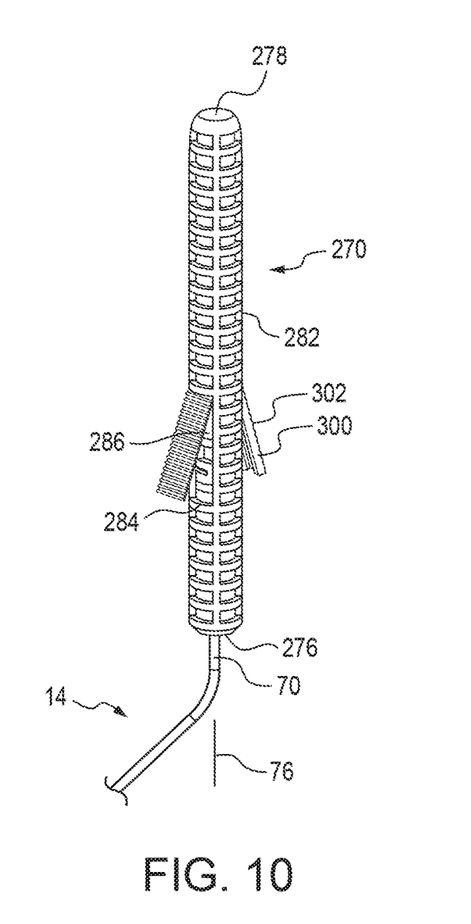
FIG. 10 is a perspective view of another handle and the proximal end portion of an elongate body of the suturing device showing another variation for the handle and an actuator for the suturing device of FIG. 1.
Figure 11:
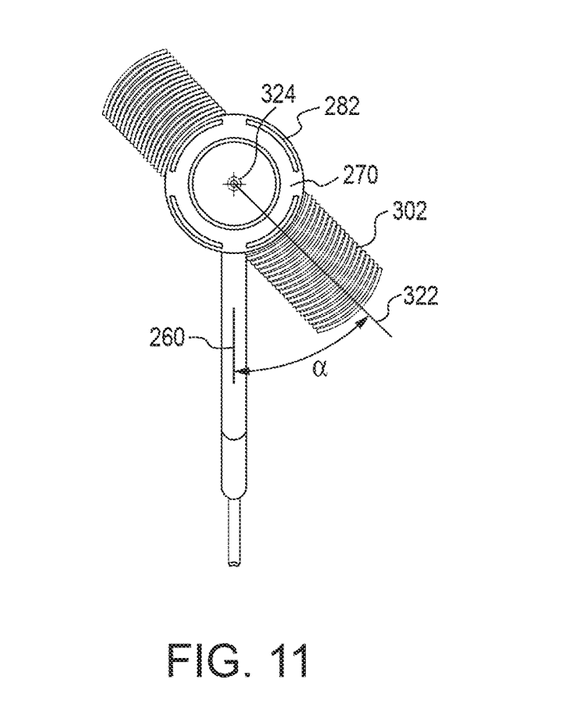
FIG. 11 is a top view of the suturing device of FIG. 1 having the handle and actuator shown in FIG. 10.
Figure 12:
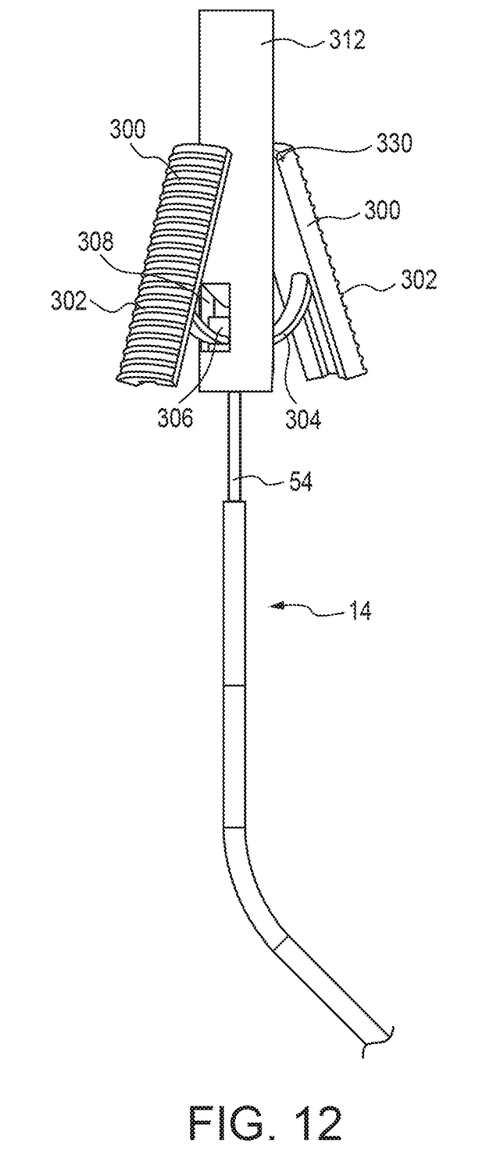
FIG. 12 is a perspective view of triggers and a slider connected with a wire and the proximal end portion of the elongate body of the suturing device of FIG. 10.

With reference to FIGS. 10-12, the suturing device 10 can include a handle 270 connected with the elongate body 14. The handle 270 connects with a proximal end portion 70 of the elongate body 14 and is fixed to the elongate body 14 such that movement of the handle 270, e.g., rotational or translational movement, results in the same movement of the elongate body 14. The handle 270 includes an elongate bore (not visible in FIGS. 10-12) in which the proximal end portion 70 of the elongate body 14 is received. The elongate bore extends from a distal handle end 276 toward a proximal handle end 278 and is aligned with the proximal end portion longitudinal axis 76. The handle 270 also defines an outer side surface 282 extending between the proximal handle end 278 and the distal handle end 276. In the illustrated embodiment, the outer side surface 282 is generally cylindrical. The maximum outer diameter of the handle 270, which can also be referred to as a width measured perpendicular to the proximal end portion longitudinal axis 76 since the handle 270 need not be circular in a cross section normal to the proximal end portion longitudinal axis 76, can be 10-20 mm.

The handle 270 includes at least one trigger opening 284 extending inwardly from the outer side surface 282 of the handle 270. Two trigger openings 284 are provided in FIGS. 10 and 11. The trigger openings 284 lead to a slider cavity 286 within the handle 270.

The actuator 12 in FIGS. 10-12 includes a manually operated member, which is a trigger 300 in this embodiment, including an operator contact surface 302 spaced from the proximal handle end 278 in a direction toward the distal handle end 276. In the embodiment depicted in FIGS. 10-12, the trigger 300 pivots with respect to the handle 270. The actuator 12 in FIGS. 10-12 includes two triggers 300, which are diametrically opposed from one another. Each trigger 300 connects or is formed with a respective flexure bearing element 304, which is more clearly depicted in FIG. 12. Each flexure bearing element 304 connects with a respective foot 306 (only one foot 306 is visible in FIG. 12). Each foot 306 is received in a respective foot recess 308 provided in a slider 312. Each flexure bearing element 304 can be a resilient living hinge that biases a respective trigger 300 radially outwardly from the proximal end portion longitudinal axis 76.

The slider 312 slides within the slider cavity 286 when the actuator 12 is moved from the first operating position toward the second operating position. Each trigger 300 is connected with the slider 312 such that pivotal movement of either trigger 300 results in translational movement of the slider 312 along the proximal end portion longitudinal axis 76.

Each trigger 300 includes a respective operator contact surface 302 that extends outwardly in a radial direction from the outer side surface 282 of the handle 270. Each respective operator contact surface 302 is positioned forwardly (toward the distal end portion 72 of the elongate body 14) from the proximal handle end 278. Each trigger 300 is also positioned between the proximal handle end 238 and the distal handle end 236.

The slider 312 is connected with the wire 54 such that movement of the slider 312 results in movement of the wire 54. Instead of connecting directly with the wire 54, the slider 312 could connect with the wire 54 through a tube, rod or other element if desired, where the slider 312 engages the tube, rod or other element, which is connected with the wire 54.

As mentioned above, the elongate body 14 can have a bayonet configuration and defines the proximal end portion longitudinal axis 76 and the distal end portion longitudinal axis 78 (see FIG. 1). With reference to FIG. 11, both the proximal end portion longitudinal axis 76 and the distal end portion longitudinal axis 78 reside in an elongate body plane 260. A line 322 emanating from the center 324 of the handle 270 through the operator contact surface 302 is offset an internal angle α from the elongate body plane 260. Alternatively, the line 322 emanating from the center 324 of the handle 270 through the operator contact surface 302 can be offset an internal angle α from the plane in which the curved needle passage radius 160 (FIG. 2) resides. Positioning the operator contact surface 302 as such locates the operator contact surface 302 away from the line of sight for the surgeon. The internal angle α depicted in FIG. 11 is about 45 degrees, however the internal angle α can be between 5 degrees and 85 degrees.

To move the actuator to the second operating position, the operator pushes the operator contact surface 302 so that the respective trigger 300 pivots about a pivot axis 330 with respect to the handle 270 toward the proximal end portion longitudinal axis 76. The pivotal movement of the trigger 300 toward the proximal end portion longitudinal axis 76 results in the flexure bearing element 304 bending and moving the foot 306 in a direction parallel to the proximal end portion longitudinal axis 76 away from proximal handle end 278 toward the distal handle end 276.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A suturing device comprising:
a handle including a proximal handle end and a distal handle end;
an elongate body connected with the handle, the elongate body including a proximal end portion and a distal end portion;
an actuator interacting with the elongate body and operable between a first operating position and a second operating position, the actuator including a trigger including an operator contact surface spaced from the proximal handle end in a direction toward the distal handle end, wherein the trigger pivots with respect to the handle, and the actuator further includes a slider connected with the trigger such that pivotal movement of the trigger results in the slider moving coaxial or parallel with a longitudinal axis of the elongate body and a flexure bearing element connecting the trigger with the slider; and
a needle holder extending away from the distal end portion or provided as part of the distal end portion of the elongate body, the needle holder including a distal end section having a distal-most tip and defining a needle passage and a distal opening adjacent the distal-most tip, the needle passage being configured to receive at least a portion of an associated needle when the actuator is in the first operating position.

2. The suturing device of claim 1, wherein the elongate body has a configuration that defines a proximal end portion longitudinal axis and a distal end portion longitudinal axis both residing in an elongate body plane, wherein a line emanating from the center of the handle through the operator contact surface is offset an internal angle between 5 degrees and 85 degrees from the elongate body plane.

3. The suturing device of claim 1, wherein the needle holder is a curved needle holder defining a curved needle passage following a curved needle passage radius, wherein a line emanating from the center of the handle through the operator contact surface is offset an internal angle between 5 degrees and 85 degrees from a plane in which the curved needle passage radius resides.

4. The suturing device of claim 1, wherein the flexure bearing element is a resilient living hinge.

5. The suturing device of claim 1, wherein the flexure bearing element biases the trigger radially outwardly from the longitudinal axis.

* * * * *